United States Patent [19]

Willis

[11] Patent Number: 5,164,413

[45] Date of Patent: Nov. 17, 1992

[54] ACNE TREATMENT

[75] Inventor: Sandra L. Willis, Somerset, N.J.

[73] Assignee: Bristol-Myers Squibb Company, New York, N.Y.

[21] Appl. No.: 704,168

[22] Filed: May 22, 1991

[51] Int. Cl.⁵ .............................................. A61K 31/19
[52] U.S. Cl. .................................... 514/557; 514/513; 514/629; 514/859
[58] Field of Search ................ 514/557, 513, 629, 859

[56] References Cited

U.S. PATENT DOCUMENTS 4,485,091  11/1984  Fitton ..................................... 424/62
4,608,370  8/1986  Aronsohn ........................... 514/159

OTHER PUBLICATIONS

Chemical Abstracts 92:53400m (1980).

Primary Examiner—Leonard Schenkman
Attorney, Agent, or Firm—Sandra M. Nolan

[57] ABSTRACT

Acne can be treated by applying to the skin of a subject a composition containing one of a certain group of acids, acid halides or amides.

4 Claims, No Drawings

ACNE TREATMENT

BACKGROUND

Acne treatments which employ highly irritating, and often unstable, substances such as hydrogen peroxide are well known. See, for example, U.S. Pat. No. 4,485,091, which discloses hydrogen peroxide-containing formulations.

In acne treatment, some controlled irritation can be beneficial to the skin in that the blemished skin "dies" after minor irritation and is replaced by healthy, fresh skin in a process known as "exfoliation". In U.S. Pat. No. 4,608,370, formulations containing—as essential ingredients—salicyclic acid, resorcinol, lactic acid and ethanol are taught to produce a "glowing" of acne-afflicted skin, followed by peeling of the dried dead skin layer and the growth of fresh new skin.

THE INVENTION

It has been discovered that certain acids, acid halides and amides are effective in compositions and methods for treating acne.

OBJECTS OF THE INVENTION

It is an object of the invention to provide compositions containing certain compounds which are useful in the treatment of acne.

It is another object of the invention to provide a method of treating acne via application, to affected areas of the skin, of compositions containing these useful compounds.

ADVANTAGES

The compositions and methods of the invention have several advantages over other systems for treating acne.

Unlike peroxide-containing formulations, use of the invention does not involve a risk of prolonged, serious irritation of the treated areas of the skin.

Furthermore, the storage, handling and other stability problems associated with the formulation and packaging of peroxide-containing products are avoided.

In addition, the systems of the invention may employ only one active ingredient. They are, thus, simpler and easier to prepare than formulations containing several active components, such as the salicyclic-acid containing compositions referred to above.

These and other objects and advantages of the inventions will be better understood after consideration of the following descriptions and claims.

DESCRIPTION OF THE INVENTION

Unless otherwise stated, all percentages recited herein are weight percentages based on total composition weight.

All publications referred to herein are hereby incorporated by reference.

THE COMPOUNDS

The compounds which function as active ingredients in the compositions and methods of the invention conform to formula I:

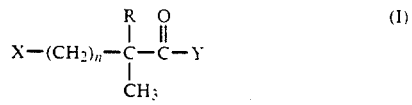

wherein
X = H or

$n = 1$, 2 or 3;
R = H or $CH_3$; and
Y = OH, Cl, Br, F, or $NH_2$.
Preferably, the compounds are of formula II or III.
Formula II compounds have the structure:

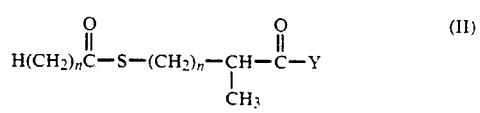

wherein
$n = 1$, 2 or 3; and
Y = OH; Cl, Br, F, or $NH_2$.

Two highly preferred compounds of formula II are those in which $n = 1$ and Y = OH or Cl, i.e., 3-(acetylthio)-2-methylpropanoic acid and its acid chloride. Of this group, the acid chloride is most preferred.

Formula III compounds conform to the structure:

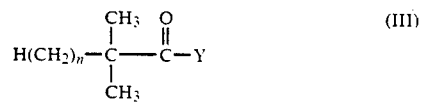

wherein
$n = 1$, 2 or 3; and
Y = OH, Cl, Br, F, or $NH_2$.

Two highly preferred compounds of formula III are those in which $n = 1$ and Y = OH or Cl, i.e., pivaloyl acid and its acid chloride. Of this group, the acid chloride is most preferred.

Mixtures are operable.

THE COMPOSITIONS

Compositions containing one or more of the new acne-treatment ingredients of the invention will generally contain the compound(s) in an effective amount for treating acne on the skin. By "effective amount(s)" is meant any suitable quantity which, when topically applied to acne afflicted skin, or epidermis, cause therapeutic exfoliation, i.e., a minor temporary redness or irritation, followed by drying and/or peeling of the treated area to leave fresh, healthy skin.

Suitable quantities of compounds of formula I, II or III in the compositions will generally lie between about 0.01 wt % and about 50.0 wt %.

The compositions of the invention may be formulated to include active ingredients other than the acids or acid halides described above. Thus, effective quantities of bacteriocides, fungicides, anti-inflammatories and the like may be used. In addition, the use of any buffers or pH modifiers necessary to stabilize such ingredients are also contemplated.

When one or more active ingredient(s) other than compounds of formula I are employed, they will usually be present in amounts suitable for their functions. Generally, concentrations of about 0.001 to about 20.0 wt % are useful.

In addition, the compositions of the invention will generally contain one or more vehicles for the active ingredient(s). Useful vehicles include water, $C_{1-6}$ alkanols and the like. Isopropanol is a preferred vehicle. Mixtures are operable.

The quantity of vehicle(s) employed is generally not critical and will depend upon the way in which the active component(s) will be applied. Thus, sprays, heated fumes, or room temperature fumes will contain suitably high concentrations (i.e., about 10–99.99 wt %) of a liquid vehicle, e.g. water or alcohol. On the other hand, a gel or cream formulation, such as one dispensed from a tube or jar, will usually contain lower concentrates (i.e., about 0.01–50 wt %) of a liquid vehicle.

Vaporous methods of treatment, i.e., those in which the active component(s) is delivered to the skin surface via air or other inert gas(es) are preferred. The amount of active compound(s) deposited on the skin is about 0.001 to about 0.5 grams per treatment.

Ampoules, or other containers, of suitable size can be used to package compositions to be used in a vapor state. Suitable containers will hold varying amounts of the composition and be adapted for spraying, painting, or otherwise contacting skin.

When a gel or ointment is desired, suitable amounts of gellants or thickeners will be present.

The use of conventional amounts of various excipients and/or formulation stabilizers is contemplated. Thus, silica, petrolatum, thickeners, surfactants, colorants, perfumes, antioxidants, chelating agents, etc. can be used in suitable amounts.

The formulations of the invention can be applied via any type of product generally used for topical application to the skin. Thus, creams, lotions, ointments, gels, masks, sprays, points, salves, powders, etc. are useful forms.

THE METHOD

Generally, the acne treatment process of the invention involves contacting the affected areas of the skin with one or more of the compositions described above for a few hours a day for about two to about three days, or as otherwise directed by a physician.

As was mentioned above, some slight irritation with concomitant itching and/or a tingling or "burning" sensation will usually occur during the first two to three days of treatment.

After the initial irritation, an apparent stimulation of mitotic activity and increased turnover of follicular epithelial cells take place. Afterwards, any comedones are extruded and subside, leaving the skin glowing and clear. Oxidation of sebaseous oils is also believed to occur.

Thus, the initial irritation phase is followed by the formation of a dead outer layer. Once the dead outer layer is gone, a layer of new, fresh skin, usually free of acne or other blemishes, evolves. The entire process, from application through development or growth of healthy skin takes from about one week to about two weeks.

If the irritation becomes too severe, one or two water rinses will generally remove the composition from the skin. Treatment should be discontinued and medical attention sought if a severe negative reaction occurs.

Contact with the eyes, mouth, angles of the nose and mucous membranes should be avoided, if possible.

EXAMPLES

The following examples illustrate the invention.

EXAMPLE 1

The entire face of a subject was exposed, at room temperature, to fumes of 3-(acetylthio)-2-methyl propanoic acid chloride. For each day, the treatment involved are one-half (½) hour contact with fumes of the acid chloride alone, followed by an additional 3 to 4 hours contact with fumes of an acid chloride/isopropanol combination (1:20 chloride: isopropanol by volume). This treatment was conducted for a total of about 3 days. Treatment was then discontinued.

After one week, the irritation which had occurred earlier during the treatment had subsided. Thereafter, mitotic activity increased, and the comedomes present were extruded and subsided, leaving the skin glowing and clear.

EXAMPLE 2

Using the undiluted acid chloride employed in Example 1, a 10 ml ampoule is filled, under nitrogen. The ampoule is opened, a funnel is placed over it, and the fumes are directed to the area to be treated by holding the open end of the funnel near the skin surface.

Because the fumes are directed to specific areas when treating using ampoules, this treatment need be performed for only a few minutes a day (i.e., less than about 20 minutes per day) until beneficial results occur.

EXAMPLE 3

A formulation containing about 50 wt % pivaloyl chloride in an isopropanol vehicle is useful, when topically applied, in a manner similar to that used in Example 1, is useful for treating skin affected with acne.

As the examples state, the 3-(acetyl thio)-2methyl propanoic acid chloride and pivaloyl chloride are useful in the treatment of facial acne.

Reasonable variations, such as those which would occur to a skilled artisan, can be made herein without departing from the scope of the invention.

What is claimed is:

1. A method of treating acne comprising the step of applying to the skin of a subject suffering from acne, a composition containing an effective amount of a compound of formula I:

$$X-(CH_2)_n-\underset{\underset{CH_3}{|}}{\overset{\overset{R}{|}}{C}}-\overset{\overset{O}{\|}}{C}-Y \qquad (I)$$

wherein
X = H or

n = 1, 2 or 3;
R = H or $CH_3$; and
Y = OH, Cl, Br, F, or $NH_2$.

2. The method of claim 1 wherein the compound employed is of formula II:
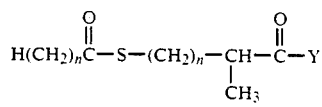
(II)
wherein
n = 1, 2 or 3; and
Y = OH, Cl, Br, F, or NH$_2$.
3. The method of claim 1 wherein the compound employed is of formula III:
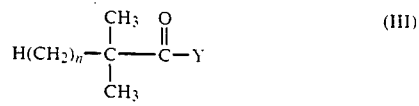
(III)
wherein
n = 1, 2 or 3; and
Y = OH, Cl, Br, F, or NH$_2$.
4. The method of claim 3 where n = 1 and Y = OH or Cl.
* * * * *